(12) United States Patent
Hagemeister et al.

(10) Patent No.: US 8,110,648 B2
(45) Date of Patent: Feb. 7, 2012

(54) SILOXANES CONTAINING METHYLOL GROUPS

(75) Inventors: Timo Hagemeister, Munich (DE); Juergen Strohrer, Pullach (DE)

(73) Assignee: Wacker Chemie AG, Munich (DE)

( * ) Notice: Subject to any disclaimer, the term of this patent is extended or adjusted under 35 U.S.C. 154(b) by 150 days.

(21) Appl. No.: 12/595,213

(22) PCT Filed: Feb. 26, 2008

(86) PCT No.: PCT/EP2008/052289
§ 371 (c)(1),
(2), (4) Date: Oct. 8, 2009

(87) PCT Pub. No.: WO2008/125379
PCT Pub. Date: Oct. 23, 2008

(65) Prior Publication Data
US 2010/0068394 A1    Mar. 18, 2010

(30) Foreign Application Priority Data

Apr. 11, 2007  (DE) .................. 10 2007 016 990

(51) Int. Cl.
*C08G 77/16* (2006.01)
*C08G 77/26* (2006.01)

(52) U.S. Cl. .......................... 528/38; 528/25

(58) Field of Classification Search ............... 528/10
See application file for complete search history.

(56) References Cited

U.S. PATENT DOCUMENTS

| 2,838,423 | A | * | 6/1958 | Giikey ............ 427/387 |
| 3,432,536 | A | * | 3/1969 | Simoneau ......... 556/419 |
| 3,461,100 | A |   | 8/1969 | Payne et al. |
| 6,803,408 | B2 | * | 10/2004 | Anderson et al. ..... 524/588 |
| 2005/0176601 | A1 | | 8/2005 | Samain et al. |
| 2006/0211587 | A9 | | 9/2006 | Samain et al. |

FOREIGN PATENT DOCUMENTS

| DE | 10047643 A1 | 4/2002 |
| EP | 0143175 A1 | 6/1985 |
| EP | 0342826 A2 | 11/1989 |
| EP | 0606532 A1 | 7/1994 |
| EP | 1544223 A1 | 6/2005 |
| EP | 1555011 A1 | 7/2006 |

* cited by examiner

*Primary Examiner* — Marc Zimmer
*Assistant Examiner* — Lindsay Nelson
(74) *Attorney, Agent, or Firm* — Brooks Kushman P.C.

(57) ABSTRACT

N-methylol-containing organosiloxane polymers further containing at least one Si-bonded N-hydrocarbyl-N-(methylol or methalkoxy)-hydrocarbyl group are storage stable and retain their ability to post-crosslink, and display excellent permanence on many substrates. They are particularly useful for the treatment of fibers, textiles, and leather.

8 Claims, No Drawings

SILOXANES CONTAINING METHYLOL GROUPS

CROSS-REFERENCE TO RELATED APPLICATION

This application is the U.S. national phase of PCT Appln. No. PCT/EP2008/052289 filed Feb. 26, 2008 which claims priority to German application DE 10 2007 016 990.8 filed Apr. 11, 2007.

BACKGROUND OF THE INVENTION

1. Field of the Invention

The present invention relates to methylolated organofunctional siloxanes, their preparation and their use as coatings and binders.

2. Description of the Related Art

Silicones and silicone-containing formulations and composites are known and are widely used in the form of films, coatings and overcoatings for modifying and enhancing a very wide range of materials of construction and fibers. Silicones and silicone-containing formulations have a performance spectrum that makes them in many respects superior to purely organic films, coatings and overcoatings. The use of silicone products thus leads to a substantial improvement in otherwise unobtainable but generally desirable properties such as for example flow behavior, gas permeability, abrasion resistance, hydrophobicity, smoothness, haptics or luster on the part of the treated substrate.

An immense problem with all coatings, but in particular with silicone coatings and their limited chemistry, is the often poor permanence on the particular treated substrate. The consequence of this poor permanence is that the coating is simple to remove mechanically, for example by rubbing or scuffing, or may become detached again from the substrate as a result of chemical stress, for example contact with various solvents and/or exposure to certain pH environments (as occur in washing operations for example).

One approach to solving the problem of poor permanence consists in crosslinking the individual silicone polymer chains with the substrate to be treated as well as with each other, and so increasing the mechanical and chemical resistance and hence permanence of the overall system.

The crosslinking between the chains and the bonding to the substrate may be affected not only via noncovalent interactions but also via covalent bonds.

Hydrogen bonds in particular have become established among the noncovalent interactions. Hydrogen bonds, formed for example in the form of urethane or urea groupings within the group of thermoplastic silicone elastomers, combine to ensure an increased network density and also, by interacting with substrate groups which likewise form hydrogen bonds (for example hydroxy units in the case of cellulose surfaces), a certain degree of fixation. The preparation and use of such thermoplastic silicone elastomers are described at length in the publications EP 0 606 532 A1 and EP 0 342 826 A2 among others.

A different noncovalent mechanism of crosslinking involves acid-base interactions between Lewis-basic/Lewis-acidic groups of the silicone polymer with Lewis-acidic/Lewis-basic groups of the substrate or of the polymer. Examples thereof are amino-functional silicone oils which, as will be known, have a positive influence on the hydrophobicity and softness of textiles in particular and, by virtue of their Lewis-basic amino groups, have the property of "going on to" the Lewis-acidic fibers. Such silicone amine oils and also their uses are described in EP 1555011 A for example.

Both mechanisms produce a permanence which is only transient and insufficient, allowing the coating to be easily removed not only mechanically but also chemically.

Appreciably better permanences are achieved when the fixing of polymer and substrate or crosslinking of polymer is effected via the formation of covalent bonds.

Covalent crosslinking can be effected for example by crosslinking the silicone polymers even as they are being prepared, by using trifunctional building blocks for example. However, the polymers thus obtained are thereby adversely affected in their processing properties (for example, melt viscosities, formability, solubility in an application auxiliary). Nor is any fixing to the substrate generally possible any longer. Therefore, subsequent fixing/crosslinking following the performance of an application step is always more sensible.

Such subsequent fixing/crosslinking can be effected for example by the presence of alkoxysilyl groups in the silicone polymer which ensure better permanence through hydrolysis and condensation with hydroxy groups of the substrate or hydroxy groups of other silicone polymers.

Such alkoxysilyl-containing silicone polymers are described in EP 1544223 A1 for example. However, the Si—O—C or Si—O-E (E=element of substrate) bonds which form on attachment to the substrate are generally hydrolysis-labile and therefore easy to open again, and therefore permanence in the aqueous environment in particular is generally not good. On the other hand, the formation of comparatively stable siloxane bonds Si—O—Si generally requires a prior treatment of the substrate with appropriate silanes.

N-Methylol crosslinking, already known in the area of the purely organic polymers, is another crosslinking mechanism. It involves the production of polymers bearing N-methylolamide groups by copolymerization with suitable monomers. These N-methylolamide groups are known to bond covalently to alcoholic groups in the absence of water at elevated temperature or, in the presence of acidic catalysts, at lower temperatures. They are similarly capable of reacting with each other and of so effecting a crosslinking of the polymer. Both cases engender covalent ether bonds which are known to be very strong and to break only under extreme physical or chemical loads. This effect is utilized for example by EP 0 143 175 A, which uses a free-radical emulsion polymerization to produce polymer dispersions which are postcrosslinkable via the methylol mechanism discussed above.

N-Methylolamide groups can in principle be prepared by reaction of amines with formaldehyde, but the reaction leads in general to polymeric condensation products which via imine intermediates leads to polymeric networks. This reaction of amines with formaldehyde has already been described: U.S. Pat. No. 3,461,100 describes condensation products of aldehydes and primary di- and monoamines. The resulting highly polymeric condensation products are discussed as protective coatings. DE 10047643 A1 describes polymeric condensation products of aldehydes and silicone amines, but which are exclusively present in highly polymeric and highly crosslinked form. The product is already highly polymeric in the as-reacted state in both references. The product is accordingly no longer present in a reactive form, such as that represented by the monoaddition product of a formaldehyde molecule onto an amine, and hence is also no longer available for descendent reactions onto substrates or post-crosslinking reactions between product molecules.

In contrast, silicones that contain N-methylolated amidic structural units are in principle capable of a postcrosslinking reaction in the sense described above.

U.S. Pat. No. 3,432,536 A describes the N-methylolation of terminal and also lateral amidoalkyl polysiloxanes by treatment thereof with aqueous formaldehyde solution in the presence of methanol to obtain not only the corresponding N-methylolamidoalkyl polysiloxanes but also the corresponding N-methylol methyl ethers. In general, however, such amide-based N-methylols and ethers thereof often display significantly reduced reactivities in the subsequent crosslinking and/or substrate fixation compared with N-methylols derived from corresponding carbamates or ureates.

SUMMARY OF THE INVENTION

The present invention provides N-methylol-containing organosiloxane polymers further containing at least one Si-bonded N-hydrocarbyl-N-(methylol or methalkoxy)-hydrocarbyl group. The polymers are easily synthesized, retain their ability to post-crosslink, and display excellent permanence on many substrates.

DETAILED DESCRIPTION OF THE PREFERRED EMBODIMENTS

The present invention thus accordingly provides organopolysiloxane compounds (M) comprising N-methylol groups and at least one Si—C-attached group of the general formula (1)

—$R^3$—N($R^4R^5$)   (1), where $R^3$ is an alkyl, cycloalkyl, alkenyl, aryl or arylalkyl radical having in each case from 1 to 20 carbon atoms wherein the hydrocarbon chain may be interrupted by nonadjacent —(CO)—, —O—, —S— or —$NR^{10}$— groups and optionally substituted with —CN or -halogen;

$R^4$ is a —$CH_2OR^6$ radical or a —CH(OH)— group which is covalently attached to $R^9$ or is an alkyl, cycloalkyl, alkenyl, aryl or arylalkyl radical which is covalently attached to $R^8$ and has in each case from 1 to 20 carbon atoms, wherein the hydrocarbon chain may be substituted by nonadjacent —(CO)—, —O—, —S— or —$NR^9$— groups and optionally substituted with —CN or -halogen;

$R^5$ is an alkyl, cycloalkyl, alkenyl, aryl or arylalkyl radical having from 1 to 20 carbon atoms, a —(CO)—$OR^7$ group or —(CO)—$NR^8R^9$ group wherein the hydrocarbon chain may be interrupted by nonadjacent —(CO)—, —O—, —S— or —$NR^{10}$— groups and optionally substituted with —CN or -halogen;

$R^6$ is a hydrogen atom, an alkyl, cycloalkyl, alkenyl, aryl or arylalkyl radical having from 1 to 20 carbon atoms wherein the hydrocarbon chain may be interrupted by nonadjacent —(CO)—, —O—, —S— or —$NR^{10}$— groups, and optionally substituted with —CN or -halogen;

$R^7$ is an alkyl, cycloalkyl, alkenyl, aryl or arylalkyl radical having from 1 to 20 carbon atoms wherein the hydrocarbon chain may be interrupted by nonadjacent —(CO)—, —O—, —S— or —$NR^{10}$ groups and optionally substituted with —CN or -halogen;

$R^8$ is an alkyl, cycloalkyl, alkenyl, aryl or arylalkyl radical having from 1 to 20 carbon atoms wherein the hydrocarbon chain may be interrupted by nonadjacent —(CO)—, —O—, —S— or —$NR^{10}$— groups and optionally substituted with —CN or -halogen and optionally covalently attached to $R^4$;

$R^9$ is a —$CH_2OR^6$ group or a —CH(OH)— group which is covalently attached to $R^4$;

$R^{10}$ is an alkyl, cycloalkyl, alkenyl, aryl or arylalkyl radical having from 1 to 20 carbon atoms wherein the hydrocarbon chain may be interrupted by nonadjacent —(CO)—, —O—, —S— or —$NR^{11}$— groups and optionally substituted with —CN or -halogen;

$R^{11}$ is an alkyl, cycloalkyl, alkenyl, aryl or arylalkyl radical having from 1 to 20 carbon atoms;

with the proviso that at least one of $R^3$ and $R^5$ bears a —(C=O)— group in direct adjacency to their shared nitrogen atom.

The N-methylolyl-containing organopolysiloxane compounds (M) are stable in storage and are postcrosslinkable via the N-methylol groups of the general formula (1) and have excellent permanence on many substrates. Many substrates require no pretreatment for this excellent permanence.

Preferably, $R^3$ comprises bivalent hydrocarbyl radicals, more preferably —$CH_2$— and —$(CH_2)_3$—.

Preferably, $R^6$ comprises a hydrogen atom or alkyl or aryl radical having in each case from 1 to 6 carbon atoms, more preferably a hydrogen atom or methyl radical.

Preferably, $R^7$ and/or $R^8$ comprise alkyl radicals having in each case from 1 to 6 carbon atoms, more preferably the methyl radical.

Preferably, $R^{10}$ comprises alkyl or aryl radicals having in each case from 1 to 6 carbon atoms, more preferably the methyl radical.

$R^{11}$ is preferably an alkyl radical having from 1 to 6 carbon atoms, particularly the methyl radical.

The N-methylolyl-containing organopolysiloxane compounds (M) preferably contain units of the general formula (2)

$R^1_a R^2_b A_c SiO_{(4-a-b-c/2)}$   (2), where $R^1$ is an alkyl, cycloalkyl, alkenyl, aryl or arylalkyl radical having from 1 to 20 carbon atoms wherein the hydrocarbon chain may be interrupted by nonadjacent —(CO)—, —O—, —S— or —$NR^{10}$— groups and optionally substituted with —CN or -halogen;

$R^2$ is an alkyl, cycloalkyl, alkenyl, aryl or arylalkyl radical having from 1 to 20 carbon atoms wherein the hydrocarbon chain may be interrupted by nonadjacent —(CO)—, —O—, —S— or —$NR^{10}$— groups and optionally substituted with —CN or -halogen;

$R^{10}$ has the meanings recited above, a is 0, 1, 2 or 3, b is 0, 1, 2 or 3, c is 0, 1, 2 or 3, and A is a group of the general formula (1), with the proviso that the sum total of a+b+c is not more than 3 and the organopolysiloxane compound has at least one unit of the general formula (2) where c is other than zero.

Preferably, $R^1$ comprises alkyl or aryl radicals having in each case from 1 to 6 carbon atoms, more preferably methyl, ethyl, vinyl or phenyl radicals.

Preferably, $R^2$ comprises alkyl or aryl radicals having in each case from 1 to 6 carbon atoms, more preferably methyl, ethyl, vinyl or phenyl radicals.

a is preferably 2 or 1, b is preferably 0, and c is preferably 0 or 1.

Halogen radicals herein are preferably fluorine, chlorine, or bromine.

The term "organopolysiloxanes" herein comprehends not only polymeric and oligomeric siloxanes, but also dimeric siloxanes.

The N-methylolyl-containing organopolysiloxane compounds (M) preferably comprise essentially linear polysiloxanes having terminal and/or lateral univalent radicals A and/or chain-internal bivalent radicals A, where A has the abovementioned meaning.

Preferably not more than 5% and particularly not more than 1% of the siloxane units in the essentially linear polysiloxanes are branching units.

The N-methylolyl-containing organopolysiloxane compounds (M) are particularly preferably those of the general formula (3)

$$A_e R^1_{3-e} SiO—(SiR^1_2 O)_m—(SiAR^1 O)_n—SiR^1_{3-e} A_e \quad (3),$$

where
A and $R^1$ have the meanings therefor recited above;
e is 0 or 1;
m is 0 or a whole number from 1 to 200;
n is 0 or a whole number from 1 to 200; and
m+n is 0 or a whole number from 1 to 400;
with the proviso that at least one A radical is present per molecule.

Preferably, in the general formula (3), the individual $(SiR^1_2 O)_n$ and $(SiAR^1 O)_n$ units form a random distribution in the molecule. m+n is preferably from 5 to 200 and more preferably from 8 to 150.

The organopolysiloxane compounds (M) are obtainable in pure form and also in the form of organic solutions or aqueous dispersions.

The present invention likewise provides a process for preparing the organopolysiloxane compounds (M) comprising N-methylol groups and at least one Si—C-attached group of the general formula (1)

$$—R^3—N(R^4 R^5) \quad (1),$$

which comprises reacting organopolysiloxane precursor compounds (V) comprising at least one group of the general formula (4)

$$—R^3—NHR^5 \quad (4),$$

with aldehyde reagents of the general formula (5)

$$O=CH—R^{12} \quad (5),$$

where $R^3$, $R^4$ and $R^5$ have the meanings recited above and $R^{12}$ has the meaning of $R^6$,
with the proviso that at least one of $R^3$ and $R^5$ bears a —(C=O)— group in direct adjacency to their shared nitrogen atom.

The group of the general formula (4) preferably contains a urea or carbamate group.

Useful aldehyde reagents include, for example, monomeric forms of formaldehyde, for example formaldehyde gas and also aqueous or organic solutions of aldehydes, and also formaldehyde in condensed form, for example in the form of paraformaldehyde, trioxane or other aldehyde condensates. It is likewise possible to use an aldehyde derivative such as glyoxal for example. $R^{12}$ is preferably hydrogen, meaning that formaldehyde is used.

The preparation of the precursor compounds (V) is known art. The precursor compounds (V) are obtainable with immense variation not only as pure substance but also in ready-produced aqueous formulations.

The N-methylolyl-containing organopolysiloxane compounds (M) are generated in their preparation either as solids, as liquids, in organic solution or in aqueous dispersion.

The preparation of the organopolysiloxane compounds (M) with an aldehyde reagent can take place continuously or batchwise not only in dispersion and in organic solution but also without a solvent. Preferably, the constituents are optimally and homogeneously commixed under the reaction conditions, any phase incompatibility between the reaction components being prevented via solubilizers where appropriate.

Preferred solubilizers are alcohols, such as isopropanol, ethers, such as tetrahydrofuran and dioxane, hydrocarbons, such as toluene and xylene, chlorinated hydrocarbons, ketones, such as acetone and methyl ethyl ketone and esters and also and mixtures thereof. Solubilizers having a boiling point or boiling point range of up to 120° C. at 0.1 MPa are preferred.

The reaction can often similarly be performed in aqueous phase when the precursor compound (V) of the organopolysiloxane compounds (M) is sufficiently dispersible in an aqueous medium. Advantageous solvent systems include mixtures of polar and/or water-miscible organic solvents with water.

Preferably, the precursor compounds (V) are dissolved in a suitable aldehyde-reagent-inert solvent and the aldehyde reagent is subsequently metered in.

Preference is likewise given to a synthesis exclusively in water in which the aldehyde reagent to be metered is aqueous and the silicone component is present as a dispersion or emulsion in water adjusted to pH between 6 and 9, particularly between 7 and 8, via acids, bases and buffer systems.

Very particular preference is given to the synthesis in a water-soluble solvent or a mixture of water and a water-soluble solvent which is subsequently solvent-exchanged for water to obtain a postcrosslinking aqueous silicone dispersion of the N-methylolyl-containing organopolysiloxane compounds (M). Subsequent emulsification of the organopolysiloxane compounds (M) is likewise possible.

The N-methylol ethers which are present in the case of $R^6 \neq$ hydrogen atom are readily obtainable from the primary methylols obtained, by consecutive etherification following methods familiar to a person skilled in the art.

The N-methylolyl-containing organopolysiloxane compounds (M) are useful in pure form or as a constituent of formulations as coatings and binders for a multiplicity of substrates, in particular fibers and textile fabrics of any kind, such as textile fibers, cellulose fibers, cotton fibers and paper fibers, and also polymeric fibers, including but not limited to olefinic fibers, polyester fibers, polyamide fibers and polyurethane fibers. The N-methylolyl-containing organopolysiloxane compounds (M) are particularly useful for treating proteinaceous and proteidic fibers and fabrics, for example hair, leather, and wool articles, preferably for the purpose of improving water-repelling properties, permanence, flexibility and abrasion resistance in very flexible and highly stressed clothing and accessories, footwear, furniture covers and automotive covers.

They are also useful for coating shaped articles and surfaces capable of chemically reacting with N-methylol functions, for example wood or woodbase materials, and also paper-coated substrates and shaped articles.

The treatment of the above substrates with the organopolysiloxane compounds (M) in pure form or as a constituent of formulations endow the treated substrate at its surface with typical silicone properties, for example hydrophobicity, antiblocking effects or softness.

All the above symbols of the above formulae each have their meanings independently. The silicon atom is tetravalent in all formulae.

Unless stated otherwise, all amounts and percentages are by weight, all pressures are 0.10 MPa (absolute) and all temperatures are 20° C.

EXAMPLES

Overview of Precursor Compound (V) and of N-Methylolyl-Containing Organopolysiloxane Compounds (M) Prepared Therefrom

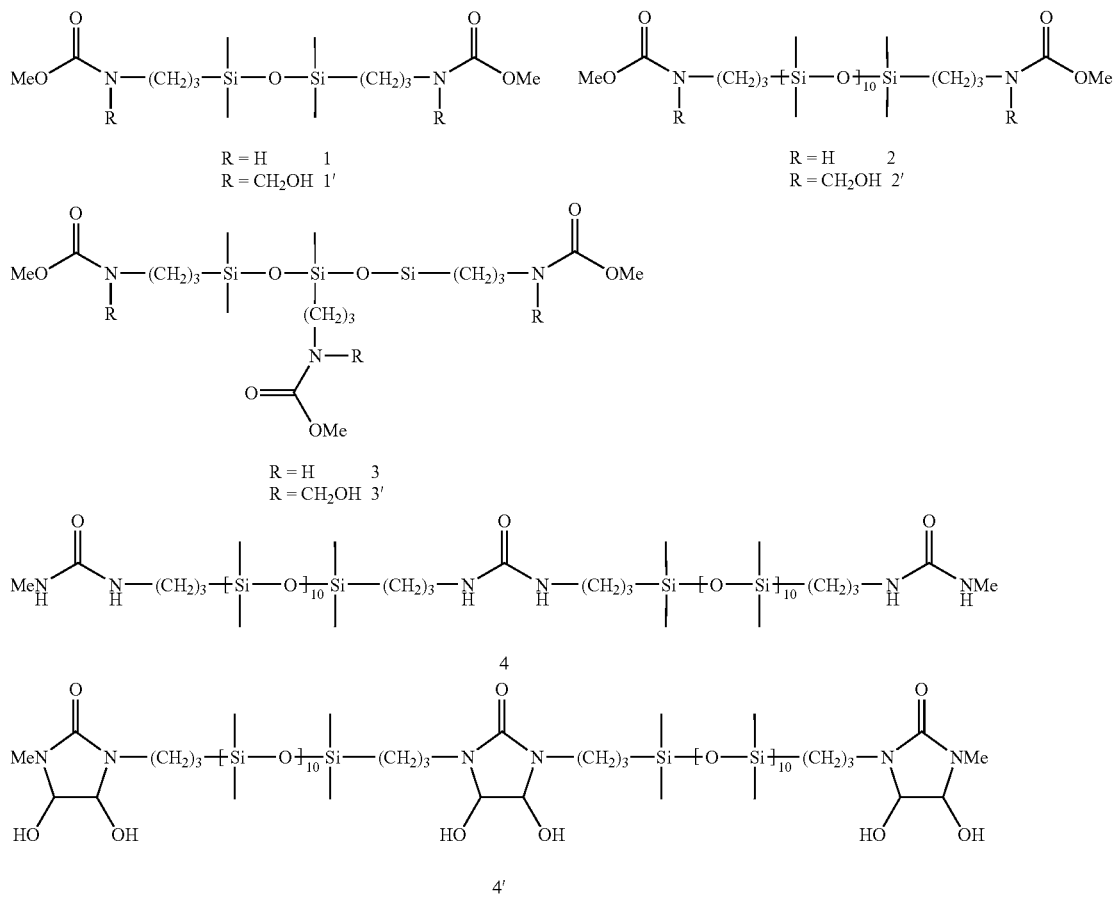

Example 1

A 250 mL round-bottom flask is charged with 50.0 g (147 mmol) of the bis(methylcarbamato)disiloxane 1 and 25.2 g (302 mmol) of 36% by weight aqueous formaldehyde solution at room temperature. The reaction mixture is stirred at 90° C. for 5 h. The product 1' obtained in the form of an aqueous solution having a content of 57.7 g (144 mmol, 98%) is stable in storage at room temperature for several weeks.

Example 2

Example 1 is repeated by suspending 100 g (78.9 mmol) of the bis(methylcarbamato)oligosiloxane 2, 20 mL of methanol and 13.3 g (160 mmol) of 36% by weight aqueous formaldehyde solution at room temperature. The reaction mixture is stirred at 100° C. for 8 h. Product 2' is obtained as an organic-aqueous solution which is stable in storage for several weeks and has a content of 97.5 g (73.4 mmol, 93%).

Example 3

Example 1 is repeated by initially charging 60.0 g (119 mmol) of the tri(methylcarbamato)trisiloxane 3 and 16.7 g (200 mmol) of 36% by weight aqueous formaldehyde solution at room temperature. The reaction mixture is stirred at 90° C. for 6 h. Product 3' is obtained as an aqueous solution which has a content of 63.6 g (107 mmol, 90%) and is stable in storage at room temperature for several weeks.

Example 4

Example 1 is repeated by adding 58.8 g (405 mmol) of a 40% by weight aqueous glyoxal solution at room temperature to 250 g (130 mmol) of the ureidosiloxane 4 in a 500 mL round-bottom flask. The reaction mixture is stirred at 95° C. for 8 h. The product 4' is obtained in the form of an aqueous solution which is stable in storage at room temperature for weeks and has a content of 266 g (127 mmol, 98%).

Example 5

In an open crystallizing dish, 1.33 g of a methanolic-aqueous solution of the methylolated bis(methylcarbamato)oligosiloxane 2' having a content of 975 mg (734 μmol) of pure substance 2' are evaporated at 140° C. for 15 min to obtain a transparent, homogeneous and flexible silicone film having a thickness of 2.0 mm.

What is claimed is:
1. N-methylol group-containing organopolysiloxane compounds comprising at least one Si—C-bonded N-methylol group of the formula (1)

$$—R^3—N(R^4R^5) \tag{1},$$

where

R³ is a divalent alkyl, cycloalkyl, alkenyl, aryl or arylalkyl radical having from 1 to 20 carbon atoms, the carbon atoms optionally interrupted by nonadjacent —(CO)—, —O—, —S— or —NR¹⁰— groups and optionally substituted with —CN or -halogen;

R⁴ is a —CH₂OR⁶ radical or a —CH(OH)— group which is covalently attached to R⁹ or is an alkyl, cycloalkyl, alkenyl, aryl or arylalkyl radical which is covalently attached to R⁸ and has 1 to 20 carbon atoms wherein the carbon atoms are optionally interrupted by nonadjacent —(CO)—, —O—, —S— or —NR⁹— groups and optionally substituted with —CN or -halogen;

R⁵ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹⁰— groups and optionally substituted with —CN or -halogen, a —(CO)—OR⁷ group or —(CO)—NR⁸R⁹ group;

R⁶ is a hydrogen atom;

R⁷ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹⁰— groups and optionally substituted with —CN or -halogen;

R⁸ is an alkyl, cycloalkyl, alkenyl, aryl or arylalkyl radical having from 1 to 20 carbon atoms wherein the carbon atoms are optionally interrupted by nonadjacent —CO)—, —O—, —S— or —NR¹⁰— groups and optionally substituted with —CN or -halogen and optionally covalently attached to R⁴;

R⁹ is a CH₂OR⁶ group or a —CH(OH)— group which is covalently attached to R⁴;

R¹⁰ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹¹— groups and optionally substituted with —CN or -halogen;

R¹¹ is an alkyl, cycloalkyl, alkenyl, aryl or arylalkyl radical having from 1 to 20 carbon atoms;

with the proviso that at least one of R³ and R⁵ bears a —(C=O)— group in direct adjacency to their shared nitrogen atom.

2. The organopolysiloxane compound of claim 1, containing units of the formula (2)

where

R¹ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹⁰— groups and optionally substituted with —CN or -halogen;

R² is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹⁰— groups and optionally substituted with —CN or -halogen;

R¹⁰ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹¹— groups and optionally substituted with —CN or -halogen;

a is 0, 1, 2 or 3, b is 0, 1, 2 or 3, c is 0, 1, 2 or 3, and

A is a group of the formula (1), with the proviso that the sum total of a+b+c is not more than 3 and the organopolysiloxane compound has at least one unit of the formula (2) where c is other than zero.

3. The organopolysiloxane compound of claim 1, comprising an organopolysiloxane compound of the formula (3)

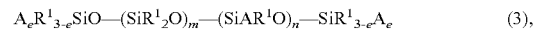

A is a group of the formula (1);

R¹ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹⁰— groups and optionally substituted with —CN or -halogen;

e is 0 or 1;

m is 0 or a whole number from 1 to 200;

n is 0 or a whole number from 1 to 200; and m+n is 0 or a whole number from 1 to 400;

with the proviso that at least one A radical is present per molecule.

4. The organopolysiloxane compound of claim 2, comprising an organopolysiloxane compound of the formula (3)

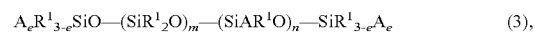

A is a group of the formula (1);

R¹ is an alkyl, cycloalkyl, alkenyl, aryl or arylalkyl radical having from 1 to 20 carbon atoms wherein the carbon atoms are optionally interrupted by nonadjacent —(CO)—, —O—, —S— or —NR¹⁰— groups and optionally substituted with —CN or -halogen;

e is 0 or 1;

m is 0 or a whole number from 1 to 200;

n is 0 or a whole number from 1 to 200; and m+n is 0 or a whole number from 1 to 400;

with the proviso that at least one A radical is present per molecule.

5. A process for preparing an organopolysiloxane compound of claim 1 comprising N-methylol groups and at least one Si—C-attached group of the formula (1)

comprising reacting at least one organopolysiloxane precursor compound (V) comprising at least one group of the formula (4)

with at least one aldehyde reagent of the formula (5)

where R¹² has the meaning of R⁶, with the proviso that at least one of R³ and R⁵ bears a —(C=O)— group in direct adjacency to their shared nitrogen atom.

6. The process of claim 5 wherein R¹² is hydrogen.

7. A coating or binder, comprising at least one N-methylolyl-containing organopolysiloxane compound of claim 1.

8. A process for treating a substrate comprising textile fibers, textile fabrics, or leather, comprising contacting the substrate with an organopolysiloxane compound of claim 1 and crosslinking the organopolysiloxane compound.

* * * * *